United States Patent [19]

Nakano et al.

[11] 4,348,477

[45] * Sep. 7, 1982

[54] METHOD FOR PREPARING A RECOMBINANT DNA PHAGE

[75] Inventors: Eiichi Nakano, Sattemachi; Tsutomu Masuda; Narimasa Saito, both of Noda, all of Japan; Danji Fukushima, Lake Genova, Wis.

[73] Assignee: Noda Institute for Scientific Research, Noda, Japan

[ * ] Notice: The portion of the term of this patent subsequent to Sep. 7, 1999, has been disclaimed.

[21] Appl. No.: 87,166

[22] Filed: Oct. 22, 1979

[30] Foreign Application Priority Data

Oct. 30, 1978 [JP] Japan ................................ 53-132631

[51] Int. Cl.³ ............................................ C12N 15/00
[52] U.S. Cl. ..................................... 435/172; 435/68; 435/235; 435/317
[58] Field of Search ................. 435/172, 68, 235, 238, 435/317

[56] References Cited

PUBLICATIONS

Murray et al., Nature, vol. 251, pp. 476–481, Oct. 1974.

Scott et al., Molecular Cloning of Recombinant DNA, pp. 133–153 (1977).

Lewin, Gene Expression-3, pp. 269, 270, 879, 886 & 901 (1977).

Thomas et al., Proc. Nat. Acad. Sci. USA, vol. 71, No. 11, pp. 4579–4583, Nov. 1974.

*Primary Examiner*—Alvin E. Tanenholtz
*Attorney, Agent, or Firm*—Schuyler, Banner, Birch, McKie & Beckett

[57] ABSTRACT

A method for preparing a novel recombinant DNA, which comprises (1) cleaving with an endonuclease a phage DNA having an endonuclease-sensitive region not in the DNA segment participating in temperate phage DNA replication and integration of DNA into a host chromosome but in other DNA segments, a temperate phage DNA having an endonuclease-sensitive region in the DNA segment carrying genetic information for the production of coat protein, and a DNA carrying the intended genetic information, (2) mixing together all fragments produced by said cleaving, (3) adding DNA ligase to the mixture, and (4) recovering from the resulting mixture a phage DNA having its coat protein producing ability deleted by the replacement of the DNA segment carrying genetic information for coat protein production with a DNA fragment carrying the intended genetic information.

11 Claims, No Drawings

METHOD FOR PREPARING A RECOMBINANT DNA PHAGE

This invention relates to a method of preparing a novel recombiant DNA.

The genetic manipulation is a new research field initiated as the result of timely union between, on the one hand, the rapid progress in the researches on genetic and chemical properties of replicons such as plasmids and bacteriophages and, on the other hand, the progress in the researches on enzymes associated with DNA (deoxyribonucleic acid), especially endonuleases which recognize the sequences of nucleotides in DNA and cause specific cleavage of nucleotide chains (restriction enzymes) and DNA-ligases.

The research on genetic manipulation is believed to lead the biology to a new and profound domain where it has been impossible to reach with conventional scientific techniques. Above all, anticipated emancipation of the gene system from its dependence on natural recombination is a problem which has attracted keen interest. Further, it is expected that such a manipulation, if fully worked out, will create microorganisms having desirable characters and in some future, along the accumulation of experiences in the fermentation industry and other branches, will be able to harness higher organisms to serve the human society.

Various procedures have heretofore been proposed for the gene recombination. For instance, there is a known procedure for the recombination of λ (lambda) phage DNA with a *Drosophila melanogaster* DNA fragment. However, since the site of recombination is the DNA region carrying the genetic information necessary for lysogenization of the phage (which means integration of the phage DNA into the host cell DNA), it becomes impossible to integrate the resulting hybrid DNA into the host DNA. Consequently, in actual practice it is necessary to preserve always the host cell and the phage for ready use, but the preservation of the phage presents a problem.

It is also known that the production of DNA ligase can be greatly increased by lysogenizing in a host a recombinant DNA carrying genetic information necessary for the lysogenization (for example, a recombinant DNA prepared by integrating the gene DNA of *E. coli* DNA-ligase into the middle segment of λ phage DNA) and continuing the cultivation of the resulting lysogen while inducing the lysogenized phage. In this case, however, there are problems such as difficult purification of the enzyme owing to the simultaneous formation of phage particles and a problem of environtal pollution with the phage; particularly, the pollution with a phage having a recombinant DNA presents an important social problem.

Further, if a host is infected with a plasmid which has been integrated with genetic information of a specific enzyme protein, production of the specific enzyme would take place continually even when the host cell is in preserved state, thus causing considerable disturbance in host metabolism and inducing various secondary variations to compensate the disturbance. For instance, some of the plasmids undergo mutation to decrease the number of copies of the plasmid, while others acquire through mutation the behavior to decrease the function or synthetic activity of the enzyme or to affect other metabolic systems so as to correct the distorted character. In actual cases, because of such secondary variations which profoundly affect the results, the genetic recombination procedure is far from being satisfactory.

Under the circumstances, the present inventors conducted an extensive investigation using bacteriophage in order to eliminate the aforementioned difficulties.

The phage particle generally consists of protein and nucleic acid (DNA or RNA), forming a structure in which the nucleic acid is surrounded by the protein (called coat protein). The nucleic acid bears in memory all of the genetic information necessary for the bacteriophage to multiply on infecting a host cell. In the case of the bacteriophage λ for example, the one half of the DNA strands carries genetic information necessary for self replication and the other half carries the genetic information for the synthesis of coat protein (A. D. Hershey, editor, "The Bacteriophage Lambda, published by Cold Spring Harbor Lab., p. 45, 1971). Accordingly, if a phage DNA segment carrying the genetic information for the synthesis of coat protein is replaced by another DNA segment carrying the genetic information, for example, for the synthesis of a useful enzyme, by the aid of endonuclease and DNA ligase, it seems possible to induce the phage, on infecting a host cell, to synthesize a large amount of the useful enzyme in place of the coat protein. However, since bacteriophage generally has endonuclease-sensitivity even in its DNA section participating in self replication, it undergoes cleavage in said segment by the action of endonuclease, and the self replication becomes impossible.

Therefore, the present inventors concentrated their efforts to the development of a method for preparing a novel recombinant DNA which has been eliminated of endonuclease-sensitivity of the DNA segment participating in self-replication while keeping the self-replicating ability intact and which, in addition, has its coat protein producing ability deleted by the replacement of its DNA segment responsible for the synthesis (production) of coat protein with a DNA fragment carrying the intended genetic information. As a result it was found that a hybrid DNA which is self-reproducible and which contains the intended genetic information in place of the coat protein producing ability can be prepared in genetic manipulation easily and efficiently by replacing the DNA region carrying genetic information for the coat protein formation with a DNA fragment carrying the intended genetic information by using a phage DNA having a region susceptible to cleavage by endonuclease not in the DNA segment participating in the replication of DNA and in the incorporation of DNA into a host chromosome but in other DNA segments, another phage DNA of the same or related species having a region cleavable by endonuclease in the DNA segment carrying genetic information for the coat protein formation, and a DNA carrying the intended genetic information. Based on this finding the present invention has been accomplished.

The purpose of the present invention is to provide a novel recombinant DNA and the process for producing the same.

Other purposes and advantages of the present invention will be apparent from the descriptions below.

According to this invention, there is provided a method for preparing a novel recombinant DNA, which comprises (1) cleaving with an endonuclease a phage DNA having an endonuclease-sensitive region not in the DNA segment participating in temperate phage DNA replication and integration of DNA into a host chromosome but in other DNA segments, a temperate phage DNA having an endonuclease-sensitive region in the DNA segment carrying genetic information for the production of coat protein, and a DNA carrying the intended genetic information, (2) mixing together all fragments produced by said cleaving, (3) adding DNA ligase to the mixture, and (4) recovering from the resulting mixture a phage DNA having its coat protein producing ability deleted by the replacement of the DNA segment carrying genetic information for coat protein production with a DNA fragment carrying the intended genetic information. The recombinant DNA obtained according to this invention can be incorporated into a host chromosome and the recombinant DNA integrated in the host can be reproduced in a large amount by induction. Since the novel recombinant DNA of this invention is deleted in the coat protein producing ability, it cannot produce an active form of phage particles and, hence, presents no pollution problem. Moreover, a DNA having a molecular weight higher than that of conventional one can be used for the DNA carrying an intended genetic information.

The invention is described below in detail.

Although bacteriophages generally multiply depending more or less on the function of their host, they are replicons capable of multiplying independently outside the host chromosome, namely, it is in the autonomous state. The bacteriophage used in this invention is a temperate phage having such property that when the phage infected a host cell, its phage DNA can be integrated in the host cell DNA (lysogeny). Preferable temperate phages are lambdoid phages including λ (IFO 20016), 434 (IFO 20018), 82 (IFO 20019), $\phi$80 (IFO 20020), $\phi$170 (IFO 20021), etc. Also usable are DNA of said phages integrated in a host DNA, such as, for example, $\phi$80 lysogenized in E. coli W3110 [E. coli K12 strain W3110 ($\phi$80) (ATCC 31277)], λcI857 lysogenized in E. coli W3350 [E. coli K12 strain W3350 (λcI 857) (ATCC 31278)], etc.

Preferred endonucleases are those of high specificity, which are capable of recognizing a specific region and cleaving the DNA double helix at the recognized region so as to form "staggered" cohesive ends. A most suitable endonuclease is a restriction enzyme such as EcoRI, Bam I, or Hind III. The restriction enzymes are available from Seikagaku Kogyo Co. or Boehringer Mannheim Yamanouchi.

The phage DNA having a region cleavable by endonuclease not in the DNA segment participating in DNA replication and integration of DNA into a host chromosome but in other DNA segments can be prepared, for example, by first preparing an endonuclease-resistant mutant phage which is absolutely uncleavable by a restriction enzyme and mating this mutant phage with a phage having a cleavable region also in the DNA segments other than the DNA segment participating in DNA replication and integration of DNA into a host chromosome.

The above-noted endonuclease-resistant phage is obtained, for example, by the alternate cultivation of a lambdoid phage in a host containing a restriction enzyme and in another host containing no restriction enzyme, said alternate cultivation resulting in extinction of a phage susceptible to the action of restriction enzyme and continuous increase in the population of a mutant difficulty susceptible to said action. By such microbial concentration, it is possible to obtain finally a phage (restriction enzyme-resistant phage) containing DNA absolutely unsusceptible to the action of restriction enzyme (i.e. DNA whose chain is perfectly uncleavable by the action of the restriction enzyme).

The resistant phage can also be obtained more speedily by partially deleting the region cleavable by the restriction enzyme and then using the microbial concentration technique. The method for partially deleting the DNA region celavable by restriction enzyme consists in isolating a deletion mutant in which the phage DNA segment including the cleavable region has been deleted. When the region cleavable by the restriction enzyme is located in a DNA segment unnecessary for the survival of the phage, the resistance of the phage against a restriction enzyme can be increased by isolating the mutant in which said segment has been deleted. Owing to the deletion of DNA segment including the cleavable region, the deletion mutant has a reduced specific gravity and an improved thermal stability. By taking advantage of these properties, the mutant can be separated from an ordinary phage culture medium, for example, by cesium chloride (CsCl) density-gradient centrifugation, whereby the separation is effected by centrifugation of the culture admixed with cesium chloride, or by heating the phage culture at about 60° C. and separating the survived phage. The separated mutant is subjected to microbial concentration by culturing the mutant alternately in a host having a restriction enzyme and another host having no restriction enzyme. In such a manner, a phage having DNA perfectly unsusceptible to the action of restriction enzyme can be obtained more quickly.

By use of the thus obtained DNA of an endonuclease-resistant phage having no region cleavable by a restriction enzyme (hereinafter this phage is referred to simply as endonuclease-resistant phage), it is possible to obtain a phage having an endonuclease-sensitive region in a DNA segment other than the DNA segment carrying necessary genetic information for the phage DNA replication and the phage DNA integration into a host chromosome. For this purpose the endonuclease-resistant phage is mated with a lambdoid phage having endonuclease-sensitive region in at least a DNA segment other than the DNA segment participating in the DNA replication and DNA integration into a host chromosome (hereinafter this phage is referred to simply as endonuclease-sensitive phage). The mating is carried out by infecting with both phages a coliform bacillus (E. coli) sensitive to said phages (namely, a coliform bacillus in which both phages can multiply). For the infection, E. coli and both phages are used in the form of suspension ($10^9$–$10^{10}$/ml) and the phage suspensions can be used each separately or in mixture. The mating is also possible by inducing an endonuclease-resistant or -sensitive phage lysogenized in E. coli strain K12 and then infecting the induced lysogen with another endonuclease-sensitive or -resistant phage. The infected E. coli is shake-cultured in a medium such as, for example, Tryptone medium (any other medium can be used so long as growth of E. coli is possible) at 37° C. for 1 to 2 hours.

For the sensitive E. coli may be used any of the K12 strains including, for example, W3110 (ATCC 27325), W3350 (ATCC 27020) and 1100 (Max Plank Institut, F.R. Germany). The E. coli may be used in the form of culture fluid or in the form of suspension prepared by centrifuging the culture fluid to remove the supernatant, suspending the sediment in a 10 mM $MgCl_2$ solution, and shaking for one hour at 37° C. The latter method is better for the adsorptive infection with phages.

In such a manner as described above, it is possible to obtain about $10^5$/ml of a phage having endonuclease-sensitive region in a DNA segment other than the DNA segment carrying genetic information necessary for the phage DNA replication and the integration of phage DNA into a host chromosome.

When a phage having DNA resistant completely to the action of endonuclease was obtained from a deletion mutant deleted of DNA segments unnecessary for the survival of the phage, if the deleted DNA segments included a DNA segment participating in the integration into a host chromosome and this segment is required to exit in the intended phage, a phage having an endonuclease-resistant DNA segment responsible for the DNA replication and an endonuclease-sensitive DNA segment responsible for the integration into a host chromosome can be obtained by mating said endonuclease-resistant deletion mutant with, for example, an immunity-variant of a parental strain used in the preparation of said deletion mutant or of a strain of the same kind, collecting heavier phage particles by the cesium chloride density gradient centrifugation, and isolating a phage strain which has not undergone immunity variation. Examples of phages undergone immunity variation are those incapable of producing a protein necessary for immunity or those incapable of manifesting immunity or capable of manifesting immunity under specific conditions owing to the variation in properties of the protein responsible for the immunity.

When the endonuclease-cleavage site in the deleted segment was not existed in the segment carrying the genetic information for the DNA integration into a host, the obtained phage as such can be used as a phage having an endonuclease-sensitive region not in the DNA segment carrying necessary genetic information for the DNA replication and the integration of phage DNA into a host chromosome but in the other segments. If the endonuclease-cleavage site was existed in the segment carrying the genetic information for the DNA incorporation into a host, the intended phage can be obtained by completely eliminating the sensitive regions by the microbial concentration technique and then mating with an endonuclease-sensitive phage. If a phage deleted of a DNA segment participating in the DNA integration into a host chromosome is used as an endonuclease-resistant phage DNA, it is possible to obtain a hybrid phage having a DNA segment from an endonuclease-sensitive phage which participates in the DNA integration into a host chromosome and having an endonuclease-cleavage site in the DNA segments other than the DNA segment carrying necessary genetic information for the DNA replication and the phage DNA integration into a host chromosome.

Isolation of the intended phage from the obtained phage mixture is effected in the following way:

As an example, let phage A and phage B be lambdoid phages; by mating endonuclease-resistant phage A with endonuclease-sensitive phage B, there is obtained a new phage in which the segment carrying genetic information for the production of coat protein is a segment of sensitive phage B and the segment carrying genetic information for the self-replication is a segment of resistant phage A. In a E. coli strain which is A-resistant and B-immune, only the new phage can grow, while other phages cannot grow. Isolation of the new phage can be effected by such a technique.

The A-resistant and B-immune E. coli is obtained in the following manner:

At first the phage A is allowed to infect E. coli cells preferably under the conditions unfavorable for lysogenization. For instance, when E. coli cells are infected with phage A mutant lacking lysogeny in a proportion of 1:100, the survived cells are those resistant to phage A. The temperate phage is generally lysogenized in E. coli cells at a certain probability and forms a turbid plaque, while the mutant lacking lysogeny forms a transparent plaque. Consequently, the phage lacking lysogeny can be obtained by collecting the phage particles in a transparent plaques. By use of the phage thus collected, the procedure for sorting out the E. coli strain resistant to phage A is simplified.

The E. coli cells thus sorted out is resistant to phage A and do not adsorb phage A by nature. The adsorption specificity depends entirely on the protein existing in the tail of the phage. Since the genetic information for the adsorption of the above phage is contained in the DNA segment participating in the production of coat protein, a phage containing the genetic information for the production of coat protein of phage A cannot be adsorbed to E. coli cells resistant to phage A and, hence, cannot enter these cells. Whether or not the host E. coli is a phage-resistant mutant can be confirmed in the following way: As an example, since an E. coli resistant to λ phage cannot utilize maltose, it is detectable by the absence of red stains on the cell when it is cultivated in a medium containing maltose and an indicator comprising methylene blue and eosine yellow.

Next, the A-resistant host is imparted with B-immunity. This can be accomplished by infecting the A-resistant host cell with a phage such as phage B, in which the genetic information controlling the immunity is carried by the DNA segment participating in self-replication, to produce a host cell in which DNA of the phage B is integrated into the host DNA. If a phage having the same immunity as that of the phage B, which had been integrated into the host cell, entered this host cell, it cannot multiply therein. To ascertain whether the DNA of phage B was integrated into the host DNA, the host cell is exposed, for example, to ultraviolet rays to induce multiplication of the phage. If the phage B is liberated on shaking-culture of the irradiated host cells, integration of the phage B DNA into DNA of the host cells is ascertained.

When the phages X and X' having the same types of immunity and coat proteins are used, the intended phage is obtained in the following manner: The phage X used to impart endonuclease resistance is a phage incapable of producing a protein responsible for the immunity or a phage incapable of manifesting immunity or capable of manifesting immunity only under specific conditions owing to variation in the properties of protein. A deletion mutant phage deleted of endonuclease-cleavage sites in the DNA segments other than the DNA segment participating in the replication of DNA of phage X and integration of said DNA into a host chromosome is separated and subjected to microbial concentration to obtain an endonuclease-resistant phage. Alternately, an endonuclease-resistant phage partially deleted of DNA segments other than the DNA segment participating in the DNA replication and the DNA integration into a host chromosome is obtained from an endonuclease-resistant phage separated from the phage X by the microbial concentration technique. The endonuclease-resistant phage thus obtained is mated with phage X' and subjected to the cesium chloride density gradient centrifugation (i.e. centrifugation after addition of cesium chloride) to separate the fraction of higher specific gravity from which an endonuclease-resistant phage having the immunity of phage X is obtained.

Next, the other temperate phage to be used is a temperate phage having an endonuclease-cleavage site (susceptible site) in the DNA segment carrying genetic information for the synthesis of coat protein and the cohesive ends at the DNA terminal is the same as those of a phage having no endonuclease-sensitive region in the DNA segment participating in the DNA replication and integration into a host chromosome.

On the other hand, the DNA (donor DNA) carrying the intended genetic information is that originated from microorganisms (bacteria, molds, yeasts), higher organisms, transducing phages, or the like. Examples of the genetic information to be incorporated in the novel recombinant DNA include cystine synthetase, suppressor gene, DNA ligase, tryptophan synthetase, gene participating in the synthesis of silkworm fibroin, gene participating in the hormone synthesis, etc.

Further, the novel recombinant DNA can be efficiently prepared by use of a transducing phage DNA prepared by integrating the intended genetic information into a phage DNA having an endonuclease-sensitive region in the DNA segment participating in the synthesis of coat protein and a phage DNA having an endonuclease-sensitive region not in the DNA segment participating in the DNA replication and integration into a host chromosome but in other segments.

In cleaving a phage DNA or a DNA carrying the intended genetic information by use of endonuclease, it is suitable to allow the enzyme to act at a DNA concentration of 20 to 200 $\mu$g/ml, an enzyme concentration of 100 to 2,000 units/ml and at a temperature of 26° to 42° C., preferably 37° C., for 10 minutes to 2 hours. The cleaving can be effected in a mixture of a phage DNA and a DNA carrying the intended genetic information.

DNA ligase is then added to a mixture of generally equal amounts (in terms of DNA) of each suspension which has been subjected to the action of endonuclease. The DNA ligase used can be *E. coli* DNA ligase, T4 phage DNA ligase, or the like. Of these, T4 phage DNA ligase is most easily available. The DNA ligase is allowed to act at a DNA concentration of 10 to 80 $\mu$g/ml, DNA ligase concentration of 1 to 10 units/ml and at a temperature of 0° to 10° C. for 1 to 14 days.

The recovery of the intended recombinant DNA from the obtained mixture of various recombinant DNA's and other substances is performed in the following way.

At first *E. coli* is lysogenized with a temperate phage having the same cohesive ends and immunity as those of the phage used in preparing the recombinant DNA but having a different attachment site (the region integrated into a host chromosome on lysogenization). The resulting *E. coli* is infected with a large amount of a temperate phage having the same cohesive ends and immunity as those of the above-noted phage but having no attachment site. The infected bacterium is mixed with the recombinant DNA and kept at 20° to 40° C. to allow the latter to be incorporated into the bacterium cell. Since the phage having the same immunity as that of the recombinant DNA has been integrated into the host, the recombinant DNA entered the cell cannot multiply and becomes readily integrated into the host chromosome.

When the donor DNA used for the recombination is originated from yeasts, bacteria, transducing phages, or the like, the separation of cells containing the intended DNA from the cells lysogenized with the recombinant DNA can be effected by collecting the cells producing the products of the intended gene. For instance, if the intended gene is a gene of tryptophan synthetase, the recombinant DNA is allowed to be integrated into *E. coli* cells incapable of synthesizing tryptophan and collecting the cells which restored the tryptophan synthesizing ability, that is, the cells capable of growing in a medium lacking tryptophan.

When the donor DNA is originated from molds or higher organisms, it is used after having been combined, by means of DNA ligase, with a gene capable of expression within *E. coli*, such as, for example, a fragment of plasmid DNA having a drug-resistant gene. The separation of the intended recombinant DNA can be achieved in this case by collecting the cells manifesting the genetic information (drug resistance).

It becomes necessary to ascertain whether or not the intended genetic information is incorporated to a phage DNA used as a vector (a DNA which can be combined with a donor DNA and used to prepare a recombinant DNA capable of autonomous replication) in place of the vector DNA segment participating in the synthesis of coat proteins. This can be accomplished by infecting the *E. coli* cells capable of producing the products of intended gene with a large amount of a phage (referred to as phage C) having the same attachment site as that of the vector phage but having different immunity, then isolation the cells lysogenized with said phage C, and examining whether or not these cells can produce the products of intended gene.

When the intended genetic information is bound to the vector phage DNA by replacing the DNA segment participating in the coat protein synthesis and lysogenized in the host, the recombinant DNA is expelled from the host chromosome owing to the lysogenization of phage C; and as the host multiplies continually, the recombinant DNA in the host becomes progressively diluted until completely disappears and becomes incapable of producing the products of intended gene.

The recombinant DNA is recovered in the following way from the cells in which is lysogenized the recombinant DNA having its DNA fragment carrying the intended genetic information replaced the DNA segment of the phage DNA participating in the coat protein synthesis.

Since the host cell contains, in addition to the recombinant DNA, another phage DNA earlier in the cell, the latter phage DNA must be removed. When there is no great difference between molecular weights of the recombinant DNA and the earlier lysogenized phage DNA, multiplication of both DNA's is induced at the same time and cultivation is continued. The recombinant DNA becomes packed in the coat protein produced according to the genetic information from the earlier lysogenized phage DNA, forming infective phage particles. Accordingly, the fluid formed by lysis contains both the earlier lysogenized phage and the recombinant phage. This lysis fluid is added to a suspension of non-lysogenic *E. coli* to infect the bacterium and a large number of bacterium cells carrying the intended genetic information are separated as mentioned above. From the cells thus separated, those not producing phage particles are collected. In order to ascertain whether the phage particles are produced or not, *E. coli* strain capable of forming a plaque by the phage particles is spread on an agar plate medium and the sample being tested is spotted thereon. After incubation, occurrence or nonoccurrence of lysis around the colony of sample cell is observed.

When the molecular weight of recombinant DNA differs greatly from that of earlier lysogenized phage DNA, the latter phage DNA can be replaced by infecting the host cell with a large amount of a phage which has different immunity but same attachment site from that of the earlier lysogenized phage and the multiplication of which is not induced in the same manner as that of recombinant DNA.

The cells thus treated are cultivated to induce replication of the recombinant DNA. As soon as the replication has been induced, the cells are infected with a mutant phage (say phage D) having the same cohesive ends as those of recombinant DNA but having different molecular weight. On cultivation the recombinant DNA is recovered as packed in coat protein produced by phage D. The resulting phage containing recombinant DNA has the same coat protein as that of phage D but has a different molecular weight and, hence, different specific gravity, separation can be effected by the cesium chloride density gradient equilibrium centrifugation.

In case the recombinant DNA has too large molecular weight to be packed in coat protein of the phage D, the cells lysogenized with the recombinant DNA are cultivated to induce replication of the recombinant DNA and the cultivation is continued to produce a large number of recombinant DNA in the cells. When DNA is extracted from the cells, DNA of the host bacterium having an extremely large molecular weight is cleft during the extraction and recovered as linear DNA fragments having open ends, while the recombinant DNA is recovered as ring molecules with closed ends. Since the linear DNA and the ring DNA can be separated by the cesium chloride-ethidium bromide density gradient equilibrium centrifugation, the recombinant DNA is easily isolated.

The novel recombinant DNA thus prepared by deleting the phage DNA segment carrying genetic information for the coat protein production and recombining with the DNA fragment carrying the intended genetic information can be preserved by infecting a host cell and integrating into the host DNA. When required, the recombinant DNA preserved in host cells can be induced to "amplify" the genetic information. When the host cells are cultured in, for example, Tryptone medium, a large amount of specific protein can be produced in accordance with the "amplified" genetic information. Thus, the industrial usefulness of this invention is believed to be very great.

The invention is illustrated below with reference to Examples, but the invention is not limited thereto.

The media used in Examples are as shown below.

(1) Tryptone-agar plate:
1% of Tryptone (Difco); 0.25% of sodium chloride; 1.2% of agar; after sterilization by autoclaving 30 ml was dispensed into each Petri dish, 9 cm in diameter.

(2) B$_1$-soft agar:
1% of Tryptone (Difco); 0.25% of sodium chloride; 5 mM of magnesium chloride; 1.5 µg/ml of vitamine B$_1$; 0.5% of agar; 3 ml was dispensed into each small test tube and sterilized by autoclaving.

(3) Tryptone medium:
1% of Tryptone (Difco); 0.25% of sodium chloride.

(4) CA plate:
0.7% of dipotassium hydrogenphosphate; 0.3% of potassium dihydrogenphosphate; 0.05% of sodium citrate; 0.01% of magnesium sulfate (MgSO$_4$.7H$_2$O); 0.1% of ammonium sulfate; 0.2% of glucose; 0.15% of acid hydrolyzate of casein; 1.5% of agar.

(5) eM-SM plate:
1.05% of dipotassium hydrogenphosphate; 0.45% of potassium dihydrogenphosphate; 0.005% of magnesium sulfate (MgSO$_4$.7H$_2$O); 0.1% of ammonium sulfate; 0.047% of sodium citrate; 0.2% of glucose; 0.01% of Difco nutrient broth; 0.01% of streptomycine sulfate; 1.5% of agar.

(6) H-trp medium:
A liquid medium. 0.1 M potassium phosphate buffer (pH 7.0); 0.015 M ammonium sulfate; 1 mM magnesium sulfate, $1.8 \times 10^{-6}$ M iron (II) sulfate; 0.2% of glucose, 0.1 mg/ml of tryptophan.

(7) I-trp medium:
0.01 M TRIS buffer (pH 7.1); $6 \times 10^{-5}$ M magnesium chloride; $6 \times 10^{-4}$ M potassium phosphate buffer (pH 7.1); $5 \times 10^{-4}$ M ammonium sulfate; $4 \times 10^{-10}$ M iron (II) sulfate; 0.2% of glucose; 0.1 mg/ml of tryptophan.

EXAMPLE 1

1. Isolation of deletion mutant phage λcI875b6042 from phage λcI875.

1-1. One platinum-loopful E. coli strain K12 W3350 (λcI857) (ATCC 31278) was inoculated into 3 ml of Tryptone medium and cultured by shaking for 16 hours at 30° C. The resulting 3 ml preculture liquor was mixed with 30 ml of Tryptone medium, cultured by shaking for 3 hours at 30° C., and then for 20 minutes at 43° C. to induce multiplication of λcI857. The cultivation was continued for further 6 hours at 30° C. until bacteriolysis had taken place and the culture liquor had become nearly transparent when the cultivation was discontinued. The culture liquor was centrifuged to remove cell fragments. The supernatant was a phage λcI857 suspension, the number of phage having been about $10^{11}$/ml.

1-2. A 0.1-ml portion of the phage λcI857 suspension was added to 5 ml of TRIS buffer (pH 8.2) containing 0.02 M ethylenediaminetetraacetic acid (EDTA), then kept at 40° C. for 10 minutes, and diluted with 0.01 M TRIS buffer (pH 7.2) containing 0.01 M magnesium chloride (hereinafter this buffer is referred to as TRIS-Mg buffer) to a final concentration of $10^7$/ml. A 0.1-ml portion of the diluted phage suspension and 0.25 ml of a stationary-culture liquor of E. coli W3110 (ATCC 27325) prepared by incubation at 37° C. for 16 hours in Tryptone medium were spread on a Tryptone-agar plate together with 3 ml of molten B$_1$-soft agar held at 46° C. and cultured at 37° C. for 5 hours. The phage on the plate was leached with 4 ml of TRIS-Mg buffer and preserved in a rubber-stoppered sterilized small test tube. Using a portion of this phage suspension, the same procedure as described above was repeated five times.

1-3. Using the phage obtained in 1-2, the same procedure as described in 1-2 was repeated four times, except that the treatment was carried out at 60° C. for 10 minutes instead of the treatment at 40° C. for 10 minutes. The resulting phage suspension was diluted to $10^3$/ml. A 0.1 ml portion of the diluted phage suspension was mixed with 0.25 ml of the above-said culture liquor of E. coli W3110, then spread on Tryptone-agar plate and cultured overnight at 37° C. The phages in one of the about 100 plaques on the plate were picked up with a bamboo spit and suspended in TRIS-Mg buffer to obtain phage strain λcI857b6042.

The deletion mutant thus obtained showed a specific gravity of 1.465 which is somewhat smaller than that of 1.493 of its parent strain λcI857 and a deletion in DNA of about 23%, as calculated from the specific gravity. In DNA of the parent phage λcI857 the number of cleavages caused by the restriction enzyme Eco RI (supplied by Seikagaku Kogyo) was five, whereas the number was three in the phage strain λcI 857b6042, as calculated from the number of survival determined by using E. coli W3110 and E. coli W3110 (RI).

E. coli W3110(RI) was isolated in the following manner: A mixture of E. coli RY-13 (supplied by H. B. Boyer of the university of california) having a drug-resistance factor RI (resistant to penicillin, streptomycin, tetracyclin and sulfamides) and E. coli W3110 (ATCC 27325) was cultured and E. coli W3110(RI) having drug-resistance factor was isolated.

2. Isolation of the phage strain λcI857b6042 RI$^r$ absolutely resistant to restriction enzyme Eco RI from the phage strain λcI857b6042.

2-1. 0.25 ml of the culture liquor of E. coli W3110 obtained as in 1-2 and 0.1 ml of a suspension of phage λcI857b6042 were mixed in 3 ml of molten B$_1$-soft agar held at 46° C. The resulting mixture was spread over a Tryptone-agar plate and cultured at 37° C. for 4 to 4.5 hours. To the plate were then added 4 ml of TRIS-Mg buffer and 3 drops of chloroform. The plate was left standing at 37° C. for 15 minutes and the supernatant was transferred by means of a pipet to a rubber-stoppered small test tube. The number of phage particles was $6 \times 10^{10}$/ml.

2-2. The number of phage particles obtained in 2-1 was measured by using E. coli W3110 (RI) containing a restriction enzyme Eco RI. [Due to the restriction enzyme, E. coli W3110 (RI) cleaves and inactivates the phage DNA intruded into the cell. Consequently, the number of phage particles measured by using E. coli W3110 (RI) is far smaller than that measured by using E. coli W3110 having no restriction enzyme. The former number was $10^8$/ml which is 1/600 of the latter number.]

In the same manner as in 2-1, a phage suspension was prepared by using 0.25 ml of the culture liquor of E. coli W3110 (RI) obtained by culturing as described in 1-2 and 0.1 ml of a phage suspension obtained by diluting the phage prepared in 2-1 with TRIS-Mg buffer to a phage particle concentration of $10^7$/ml, as measured by using the strain W3110 (RI).

2-3. The phage obtained in 2-2 was treated by the procedure of 2-1. In this way, the treatment was repeated ten times by using alternately the procedures of 2-1 and 2-2. The final treatment was carried out by using the procedure of 2-1. A sample of the finally obtained phage suspension showed substantially the same number of phage particles as measured by using either the strain W3110 (RI) or the strain W3110, indicating that the phage suspension consisted of a mutant strain absolutely resistant to Eco RI. This phage suspension was diluted to the phage number of $10^3$/ml and a 0.1 ml of the diluted suspension was mixed with 0.25 ml of the culture liquor of the strain W3110. The resulting mixture was spread over the Tryptone-agar plate so as to form plaques not overlapping one another. From the plaques thus formed, a phage strain λcI857b6042 RI$^r$ absolutely resistant to Eco RI was isolated.

3. Preparation of λcI857sRIλ$_3$°sRIλ$_2$°sRIλ$_1$° having sensitivity to the restriction enzyme Eco RI in the DNA middle segment from strain λcI857b6042 RI$^r$ and wild-type λ.

3-1. Mating of λcI857b6042 RI$^r$ with λ.

0.2 ml of λcI857b6042 RI$^r$ phage suspension ($3.6 \times 10^9$/ml), 0.2 ml of λ phage suspension ($3.5 \times 10^9$/ml; a suspension prepared by culturing E. coli W3110 (λ) in 15 ml of Tryptone medium while shaking at 37° C. until the number of bacterium had reached $10^9$/ml, then transferring the culture liquor into a Petri dish, 9 cm in diameter, exposing the culture liquor to a 15 W ultraviolet lamp at a distance of 50 cm for 2 minutes 12 seconds to induce multiplication of λ phage, and continuing the cultivation for further 3 hours while shaking) and 0.2 ml of a suspension of E. coli 1100 (a bacterium suspension obtained by culturing E. coli 1100 in 15 ml of Tryptone medium while shaking until the number of bacterium reached $3 \times 10^8$/ml, collecting the bacterium cells by centrifuging, suspending the cells in 5 ml of TRIS-magnesium buffer, and shaking at 37° C. for 1 hour) were mixed and the mixture was left standing at 37° C. for 10 minutes. 0.1 ml of the resulting mixture was added to 10 ml of Tryptone medium and cultured by shaking at 37° C. for 100 minutes to obtain a phage culture liquor.

3-2. Fractionation of phage particles by cesium chloride (CsCl) density gradient centrifugation.

The phage suspension prepared in 3-1 contains λcI857b6042 RI$^r$, λ and their hybrids. In order to remove λcI857b6042 RI$^r$, the phage suspension was subjected to cesium chloride density gradient centrifugation which is an effective means to separate high polymers of different specific gravities. Since λcI857b6042 RI$^r$ has lower specific gravity than that of λ, it can be removed by collecting heavier phage particles after centrifuging.

The phage suspension obtained in 3-1 was diluted 30-fold with TRIS-Mg buffer. A 0.69 ml portion of the diluted suspension was placed in an ultracentrifuge tube, admixed with 2.3 ml of a cesium chloride solution of a specific gravity of 1.6, superposed with liquid paraffin to fill the tube, and centrifuged in a swinging rotor at 25,000 rpm for 24 hours. After centrifugation, a small hole was drilled through the bottom of the tube so that the centrifuged suspension may be discharged drop by drop. Each 3 drops were successively collected in small test tubes. The phage was detected in the fractions collected in 11th to 14th and 16th to 20th test tubes. 0.1 ml of the fraction in 12th test tube (containing phages of higher specific gravity) was dialyzed successively against 1 M KCl, 0.3 M KCl and 0.1 M KCl. 0.05 ml of the dialyzed suspension was mixed with 0.1 ml of the E. coli 1100 suspension ($2 \times 10^9$/ml), admixed with 3 ml of molten B$_1$-soft agar (46° C.), and spread over a Tryptone-agar plate. When cultured overnight at 38° C., there appeared on the plate about 5,000 opaque plaques and 50 clear plaques. The phage forming opaque plaques was wild-type λ phage, while the phage forming clear plaques seemed to be a hybrid, because the latter phage showed both properties of λcI857b6042 RI$^r$ (clear plaque) and wild-type λ (higher specific gravity).

Phage particles were picked up by means of a bamboo spit from 12 clear plaques and suspended in each 5 ml of TRIS-Mg buffer and diluted 100-fold with the same buffer. 0.1 ml of the diluted suspension, 0.1 ml of E. coli 1100 suspension and 3 ml of molten B$_1$-soft agar (46° C.) were spread over a Tryptone-agar plate and cultured overnight at 38° C. to form plaques. This procedure was repeated once more and phage particles were picked up by means of a bamboo spit from the formed plaques. The phage particles were added to 0.1 ml of TRIS-Mg buffer, admixed with 0.25 ml of E. coli 1100 suspension ($2 \times 10^9$/ml) and 3 ml of molten $B_1$-soft agar (46° C.) and spread over a Tryptone-agar plate. After culturing at 37° C. for 4 hours, 4 ml of TRIS-Mg buffer and 3 drops of chloroform were added to the plate and left standing at 37° C. for 15 minutes. The supernatant was transferred by means of a pipet to a rubber-stoppered small test tube and preserved as a stock phage suspension.

By using E. coli 1100 and Tryptone medium, a large amount of the phage were cultured and purified by means of the cesium chloride density gradient centrifugation. The phage DNA was cleft by the restriction enzyme Eco RI of E. coli and examined by the agarose electrophoresis. It was found that two of the 12 strains had two cleavage sites in the middle segment of DNA. One of such strains, $\lambda$cI857sRI$\lambda_3$°sRI$\lambda_2$°sRI$\lambda_1$°, was used in subsequent experiments as a phage containing DNA which has endonuclease-sensitive regions not in the DNA segment participating in the replication of temperate phage DNA and the integration of the DNA into a host chromosome but in other segments.

4. Separation of transducing phage $\phi$80ptrp which is phage $\phi$80 incorporated with an intended genetic information (tryptophan synthetase).

Phage $\phi$80 lysogenizes near the segment (tryptophan operon) carrying genetic information for the synthesis of tryptophan synthetase on the chromosome of E. coli. In inducing multiplication of the phage by exposing $\phi$80 lysogen to ultraviolet rays, there appears a $\phi$80 phage integrated with tryptophan operon, though the frequency level is low. By isolating such a phage $\phi$80, a transducing phage $\phi$80ptrp which is useful in subsequent experiments as a temperate phage having an endonuclease-sensitive region in the DNA segment carrying genetic information for the production of coat protein and as a DNA donor carrying the intended genetic information could be obtained.

E. coli strain K12 $B_4$ trp$^-$(obtained from Stamford University, U.S.A.), which is a strain lacking of the ability for synthesizing tryptophan synthetase, was inoculated into 15 ml of Tryptone medium, cultured by shaking at 37° C. for 4 hours, centrifuged, and suspended in 15 ml of TRIS-Mg buffer. To 1 ml of the resulting suspension, was added 0.12 ml of a suspension ($2.2 \times 10^{10}$/ml; filtered through a membrane filter) of phage $\phi$80 [prepared by the ultraviolet ray induction from E. coli strain K12 W3110 ($\phi$80) (ATCC 31277), a lysogen having tryptophan synthesizing ability]. After having been left standing at 37° C. for 15 minutes, 0.1 ml of the resulting mixture was spread over a CA plate and cultured at 37° C. for 7 to 14 days. The bacterium cells were picked up by means of a bamboo spit from the colony which was formed, then suspended in 4 ml of TRIS-Mg buffer, admixed with 2 drops of chloroform, and shaken vigorously. The resulting suspension was diluted 100-fold with TRIS-Mg buffer. 0.05 ml of the diluted suspension was mixed with 0.1 ml of E. coli 1100 suspension ($2 \times 10^9$/ml), then admixed with 3 ml of $B_1$-soft agar (46° C.) and spread over a Tryptone-agar plate. After cultivating overnight at 37° C. the phage was picked up by means of a bamboo spit from the formed plaques and inoculated into an eM-SM plate which had been sprayed with 0.1 ml of a suspension ($10^9$/ml) of E. coli K12 $B_4$trp$^-$SM$^r$ [a streptomycine-resistant strain isolated from the colony grown on cultivating E. coli K12 $B_4$trp$^-$ on an agar plate containing streptomycine] and 3 ml of 0.6% agar solution (46° C.). The plate was then incubated at 37° C. Since the eM-SM plate contained only a small amount of tryptophane which is necessary for the growth of E. coli K12 $B_4$trp$^-$ $SM^r$, only a small amount of bacterium cells grew on the plate. When the inoculant phage has tryptophan synthesizing ability, there will be formed around the plaque a ring of said bacterium grown by utilizing tryptophan produced by the inoculant phage. Therefore, the phage producing such a ring was picked up by means of a bamboo spit and purified by the treatment described in 3-2 to obtain a phage stock suspension which was used in subsequent experiments as transducing phage $\phi$80 ptrp.

5. Preparation of recombinant DNA from $\lambda$cI857-sRI$\lambda_3$°sRI$\lambda_2$°sRI$\lambda_1$° DNA and $\phi$80 ptrp DNA.

5-1. Cleaving of DNA with restriction enzyme Eco RI.

Each of the purified phage suspensions obtained in 3 and 4 was diluted with a buffer solution comprising 0.01 M TRIS-HCl (pH 8.0), 1 mM magnesium chloride and 0.1 mM ethylenediaminetetraacetic acid so that the optical density at 260 m$\mu$ may become 8. 0.5 ml of the diluted suspension was dialyzed at 24° C. for 16 hours against 100 to 150 ml of 0.1 M TRIS buffer solution (pH 8.5) containing 50% formamide and 10 mM ethylenediaminetetraacetic acid to extract DNA. The extracted DNA was further dialyzed four times at 4° C. against 150 ml of 0.1 M TRIS buffer solution (pH 7.5) containing 0.1 mM ethylenediaminetetracetic acid to obtain preparation of each DNA.

Each DNA preparation was diluted with 0.1 M TRIS buffer (pH 7.5) containing 0.1 mM ethylenediaminetetracetic acid so that the concentration may become 40 $\mu$g/ml (for $\lambda$cI857sRI$\lambda_3$°sRI$\lambda_2$°SRI$\lambda_1$° DNA) or 80 $\mu$g/ml (for $\phi$80ptrp DNA). 90 $\mu$l of each DNA solution was placed in a small test tube, admixed with 10 ml of 0.1 M magnesium chloride and 2 $\mu$l (in the case of $\lambda$cI857sRI$\lambda_3$°sRI$\lambda_2$°sRI$\lambda_1$° DNA) or 3 $\mu$l (in the case of $\phi$80 ptrp DNA) of restriction enzyme Eco RI (produced by Miles Lab. and supplied by Seikagaku Kygyo Co.) and left standing at 37° C. for one hour to effect cleaving of DNA. Thereafter, each DNA solution was heated at 73° C. for 10 minutes and quickly cooled to 0° C. to inactivate Eco RI.

5-2. Preparation of recombinant DNA.

Each 25 $\mu$l of $\lambda$cI857sRI$\lambda_3$°sRI$\lambda_2$°sRI$\lambda_1$° DNA and $\phi$80 ptrp DNA both cleft with the restriction enzyme were mixed, added with 20 $\mu$l of distilled water, 10 $\mu$l of 50 mM magnesium chloride, 10 $\mu$l of 0.1 M dithiothreitol, 10 $\mu$l of 1 mM ATP and 1 $\mu$l of $T_4$ ligase (produced by Miles Lab. and supplied by Seikagaku Kygyo Co.) and left standing for 3 days at 0° C. to obtain a liquor containing a recombinant DNA. $T_4$ ligase is an enzyme having a function of joining DNA fragments. Therefore, it is possible to prepare a recombinant by the action of this enzyme from two kinds of DNA cleft by a restriction enzyme.

6. Isolation of recombinant DNA.

E. coli K12 $B_4$ trp$^-$ ($\lambda$cI857RI$^r$h80), which is a strain derived from E. coli K12 $B_4$ trp$^-$, a tryptophan-requiring strain, by lysogenization with $\lambda$cI857RI$^r$h80 (ATCC 31285), is inoculated into 10 ml of H-trp medium and precultured at 30° C. for 20 hours. 0.5 ml of the preculture liquor was inoculated into 10 ml of a fresh H-trp medium and cultured by shaking at 30° C. When the number of cells had reached $5\times10^8$/ml, the culture liquor was cooled in ice. 6 ml of the cooled culture liquor was centrifuged (10,000 rpm, 20 minutes) and the cells were suspended in 1.5 ml of I-trp medium (0° C.). The resulting suspension was kept at 30° C. for 12 minutes and then at 0° C. for 6 minutes. To the suspension was added 1.5 ml of a suspension ($2\times10^{10}$/ml) of phage $\lambda b_2$ (a temperate phage having no attachment site to a host chromosome; supplied by National Institute of Health, Japan) in I-trp medium. After culturing at 30° C. for 12 minutes, the mixture was cooled to 0° C., then centrifuged and again suspended in 1.5 ml of 0.01 M TRIS buffer (pH 7.5) containing 0.01 M magnesium chloride and 0.01 M calcium chloride. The normal *E. coli* cannot incorporate an external DNA into the cell, whereas when treated as described above, it becomes possible to incorporate a lambdoid phage DNA into the cell.

The liquor containing recombinant DNA prepared in 5-2 was heated at 73° C. for 10 minutes and cooled quickly. 5 $\mu$l of the cooled liquor was added to 0.1 ml of 0.01 M TRIS buffer (pH 7.5) containing 0.01 M magnesium chloride and 0.01 M calcium chloride. To the resulting mixture kept at 0° C., was added 0.2 ml of a suspension of *E. coli* K12 $B_4$ trp$^-$($\lambda$cI857RI'h80) which had been treated as described above. The mixture was kept at 30° C. for 40 minutes to incorporate the recombinant DNA into the bacterial cell. After addition of 3 ml of CA-soft agar (same composition as that of CA plate, except that the agar content was 0.5%), the mixture was spread over a CA plate. After incubation for 3 to 7 days at 30° C., there were obtained 30 colonies. From the 30 colonies, those which showed no lysis in the peripheral zone were separated. From the separated colonies, two bacterial strains showing no growth on a CA plate when precultured on a Tryptone-agar plate at 42° C. were isolated.

The two strains obtained above were tryptophannon-requiring but when the lysogenized phage was removed by culturing at 42° C., they became tryptophanrequiring. Therefore, these strains were *E. coli* K12 $B_4$trp$^-$($\lambda$cI857RI'h80, $\lambda$cI857sRI$\lambda_3$°sRI$\lambda_2$°sRI$\lambda_1$° dtrp) which became tryptohan-nonrequiring by integrating a new recombinant DNA into the host DNA. This new recombinant DNA is constructed by recombination of a DNA fragment from $\lambda$cI857sRI$\lambda_3$°sRI$\lambda_2$°sRI$\lambda_1$° carrying all genetic information except for that coding for the synthesis of coat proteins with a DNA fragment from $\phi$80ptrp including tryptophan operon in such a form that the DNA segment of $\lambda$cI857sRI$\lambda_3$°sRI$\lambda_2$°sRI$\lambda_1$° DNA which participates in the synthesis of coat proteins is replaced by a DNA fragment participating in the synthesis of tryptophan synthetase and a DNA fragment having a cohesive end originated from $\phi$80ptrp DNA.

EXAMPLE 2

$\lambda$cI857sRI$\lambda_3$°sRI$\lambda_2$°sRI$\lambda_1$° and $\phi$80ptrp were prepared by the same procedures as described in paragraphs 1 to 4 of Example 1.

5-1. Cleaving of DNA with restriction enzyme Eco RI.

Purified phages obtained in paragraphs 3 and 4 described in Example 1 and a phage derived from $\phi$80 (ATCC 31277) were treated as described in Example 1 to obtain each DNA preparation.

Each DNA preparation was diluted with 0.1 M TRIS buffer (pH 7.5) containing 0.1 mM ethylenediaminetetraacetic acid to a concentration of 40 $\mu$g/ml ($\lambda$cI857-sRI$\lambda_3$°sRI$\lambda_2$°sRI$\lambda_1$° DNA) or 80 $\mu$g/ml ($\phi$80 DNA and $\phi$80ptrp DNA). To 90 $\mu$l of the diluted DNA placed in a small test tube, were added 10 $\mu$l of 0.1 M magnesium chloride and 2 $\mu$l (in the case of $\lambda$cI857sRI$\lambda_3$°sRI$\lambda_2$°sRI$\lambda_1$° DNA) or 3 $\mu$l (in the cases of $\phi$80 DNA and $\phi$80ptrp DNA) of restriction enzyme Eco RI (produced by Miles Lab. and supplied by Seikagaku Kogyo Co.). Each mixture was left standing for one hour at 37° C. to cleave the DNA, then heated at 73° C. for 10 minutes and quickly cooled to 0° C. to inactivate Eco RI.

5-2. Preparation of recombinant DNA.

25 $\mu$l of cleft $\lambda$cI857sRI$\lambda_3$°sRI$\lambda_2$°sRI$\lambda_1$° DNA, 12 $\mu$l of cleft $\phi$80 DNA and 12 $\mu$l of cleft $\phi$80ptrp DNA were mixed together. To the mixture were added 20 $\mu$l of distilled water, 10 $\mu$l of 50 mM magnesium chloride, 10 $\mu$l of 0.1 M dithiothreitol, 10 $\mu$l of 1 mM ATP, and 1 $\mu$l of T$_4$ ligase (produced by Miles Lab. and supplied by Seikagaku Kogyo Co.). The resulting mixture was left standing at 0° C. for 3 days to yield a recombinant DNA. The recombinant DNA was treated as described in Example 1 and a strain of *E. coli* K12 $B_4$trp$^-$ ($\lambda$cI857RI'h80, $\lambda$cI857sRI$\lambda_3$°sRI$\lambda_2$°sRI$\lambda_1$° dtrp) was isolated from 50 colonies.

What is claimed is:

1. A method for preparing a novel recombinant DNA, which comprises (1) cleaving with an endonuclease a phage DNA having an endonuclease-sensitive region not in the DNA segment participating in temperate phage DNA replication and integration of DNA into a host chromosome but in other DNA segments, a temperate phage DNA having an endonuclease-sensitive region in the DNA segment carrying genetic information for the production of coat protein, and a DNA carrying intended genetic information, (2) mixing together all fragments produced by said cleaving, (3) adding DNA ligase to the mixture, and (4) recovering from the resulting mixture a phage DNA having its coat protein producing ability deleted by the replacement of the DNA segment carrying genetic information for coat protein production with a DNA fragment carrying the intended genetic information.

2. A method according to claim 1, wherein the temperate phage is a lambdoid phage.

3. A method according to claim 2, wherein the lambdoid phage is lamda (IFO 20016) 434 (IFO 20018), 82 (IFO 20019), $\phi$80 (IFO 20020), $\phi$170 (IFO 20021), *E. coli* K12 strain W3110 ($\phi$80) (ATCC 31277) or *E. coli* K12 strain W3350 ($\lambda$cI857) (ATCC 31278).

4. A method according to claim 1, wherein the phage DNA having an endonuclease-sensitive region not in the DNA segment participating in temperate phage DNA replication and integration of DNA into a host chromosome but in other DNA segments is a DNA obtained by mating an endonuclease-resistant temperate phage with an endonuclease-sensitive temperate phage.

5. A method according to claim 1, wherein the DNA carrying intended genetic information is a DNA originated from molds, higher organisms or transducing phages.

6. A method according to claim 1, wherein the temperate phage DNA having an endonuclease-sensitive region in the DNA segment carrying genetic information for the production of coat protein and the DNA carrying the intended genetic information are transducing phage DNA into which the intended genetic information has been introduced, respectively.

7. A method according to claim 1, wherein the endonuclease is a restriction enzyme.

8. A method according to claim 7, the restriction enzyme is Eco RI, Bam I or Hind III.

9. A method according to claim 1, wherein the DNA ligase concentration is 1 to 10 units/ml to the DNA concentration of 10 to 80 µg/ml.

10. A method according to claim 1, wherein the DNA ligase is *E. coli* DNA ligase or T$_4$ phage DNA ligase.

11. A method according to claim 9, wherein the mixture is kept at 0° to 10° C. for 1 to 14 days.

* * * * *